United States Patent
Martin et al.

(10) Patent No.: US 9,897,560 B2
(45) Date of Patent: Feb. 20, 2018

(54) SCREENING OF ELECTRONIC COMPONENTS FOR DETECTION OF COUNTERFEIT ARTICLES USING AUTOMATED INSPECTION SYSTEM

(71) Applicant: Raytheon Company, Waltham, MA (US)

(72) Inventors: Dylan W. R. Martin, Tucson, AZ (US); Edmundo M. Samaniego, Tucson, AZ (US); John O. Crawford, Vail, AZ (US); Emmanuel J. Simeus, Tucson, AZ (US); James E. Faoro, Tucson, AZ (US)

(73) Assignee: Raytheon Company, Waltham, MA (US)

( * ) Notice: Subject to any disclaimer, the term of this patent is extended or adjusted under 35 U.S.C. 154(b) by 222 days.

(21) Appl. No.: 14/570,581

(22) Filed: Dec. 15, 2014

(65) Prior Publication Data

US 2016/0169818 A1    Jun. 16, 2016

(51) Int. Cl.
*G01N 23/223* (2006.01)
*G06K 9/00* (2006.01)
*H01L 23/544* (2006.01)

(52) U.S. Cl.
CPC ....... *G01N 23/223* (2013.01); *G06K 9/00577* (2013.01); *H01L 23/544* (2013.01);
(Continued)

(58) Field of Classification Search
CPC ................ G01N 23/223; H01L 23/544; H01L 2223/54406; H01L 2223/54473
(Continued)

(56) References Cited

U.S. PATENT DOCUMENTS 6,791,339 B2 *  9/2004  Licini .................... G01N 22/00
                                                              324/642
2006/0187719 A1  8/2006  Matsumoto et al.
(Continued)

FOREIGN PATENT DOCUMENTS

DE   10-2010-011066   9/2011

OTHER PUBLICATIONS

International Search Report and Written Opinion issued for PCT/US2015/055693 dated Feb. 3, 2016, 12 pgs.
(Continued)

*Primary Examiner* — Jeff Natalini

(57) ABSTRACT

A method includes selecting one or more analysis algorithms to be used to verify an authenticity of an electronic component. Each analysis algorithm identifies a type of data to be analyzed and/or a manner in which the data is to be collected. Each analysis algorithm also defines how the data is to be analyzed to verify the authenticity of the electronic component. The method also includes obtaining data associated with the electronic component. The method further includes analyzing the data associated with the electronic component using the one or more selected analysis algorithms to determine whether the electronic component is authentic. In addition, the method includes generating an output based on the analysis. One or more characteristics of the electronic component could be compared against one or more characteristics of at least one reference component, or variations in one or more characteristics of multiple electronic components could be identified.

21 Claims, 8 Drawing Sheets

(52) U.S. Cl.
CPC ............... *H01L 2223/54406* (2013.01); *H01L 2223/54433* (2013.01); *H01L 2223/54473* (2013.01); *H01L 2924/0002* (2013.01)

(58) Field of Classification Search
USPC ............... 324/750.01–765.01, 158.1; 702/81
See application file for complete search history.

(56) References Cited

U.S. PATENT DOCUMENTS

| | | | | |
|---|---|---|---|---|
| 2007/0223119 | A1* | 9/2007 | Takahashi | G02B 17/0657 359/859 |
| 2008/0169831 | A1* | 7/2008 | Lu | G01R 31/2886 324/750.03 |
| 2009/0099830 | A1* | 4/2009 | Gross | G01R 31/2813 703/14 |
| 2010/0237854 | A1* | 9/2010 | Kumhyr | G01R 33/10 324/750.3 |
| 2011/0220560 | A1* | 9/2011 | Verdegan | G06Q 10/06 210/90 |
| 2012/0124385 | A1* | 5/2012 | Klasen | H04L 9/3236 713/179 |
| 2013/0022167 | A1 | 1/2013 | Cardoso et al. | |
| 2015/0117701 | A1 | 4/2015 | Ross et al. | |
| 2015/0234006 | A1* | 8/2015 | Richards | G01R 31/308 324/756.02 |

OTHER PUBLICATIONS

"TruView Hawk, Automated Optical Inspection", Creative Electron, Nov. 2014, 2 pages.
Griffin Lemaster, et al., "The Economics of Die Attach Voiding in LED Assemblies", Creative Electron, Inc., Jun. 2014, 5 pages.
Dr. Bill Cardoso, et al., "WISE: Wavelet Image Spectra Enhancement of X-Ray Images", May 2014, 3 pages.
"10 ways to find counterfeit components using x-rays", Creative Electron, Nov. 2014, 15 pages.
"Algorithms: The Next Frontier for X-Ray Inspection", Creative Electron, Nov. 2014, 18 pages.
"ZVS-200S, Zyco Corporation's HVM in-tray inspection solution for FC-BGA", Zygo Corporation, 2012, 2 pages.
"KLA Tencor", 2009, 6 pages.
Kristen Stone, et al., "Automated Model-Based Inspection System for Screening Electronic Components," U.S. Appl. No. 15/288,245, filed Oct. 7, 2016, 56 pages.

* cited by examiner

SCREENING OF ELECTRONIC COMPONENTS FOR DETECTION OF COUNTERFEIT ARTICLES USING AUTOMATED INSPECTION SYSTEM

TECHNICAL FIELD

This disclosure is generally directed to the detection of counterfeit articles. More specifically, this disclosure is directed to the screening of electronic components for the detection of counterfeit articles using an automated inspection system.

BACKGROUND

A growing problem worldwide involves counterfeit electronic components, such as counterfeit integrated circuit chips. For example, a counterfeiter may sand off the top surface of an integrated circuit chip, cover the chip with a new top surface, print new markings on the chip, and try to pass off the chip as a new or different type of chip. This process is commonly referred to as "blacktopping" since the new top surface placed on the integrated circuit chip is typically black. As another example, a counterfeiter may remove an integrated circuit chip from a circuit board, "relead" the chip using new electrical leads, and try to pass off the chip as a new chip.

The counterfeiting of electronic components is becoming more and more sophisticated. It is therefore becoming more and more difficult to detect when electronic components being bought or sold are counterfeit. The potential monetary losses associated with buying or selling counterfeit electronic components could easily reach into the millions of dollars.

Conventional approaches for detecting counterfeit electronic components often fall into one of two categories. In the first category, human inspectors compare components to a known "good" reference component. Unfortunately, these approaches are often limited to a single inspection technique and small sample sizes, are subject to human error, and require lengthy inspection times. In the second category, internal structures of the electronic components can be analyzed using various inspection techniques. However, these approaches may result in the destruction of the components being tested and are therefore limited to small sample sizes.

As a particular example of a conventional approach, some inspection systems rely on X-ray imaging of integrated circuit chips. X-rays pass through an integrated circuit chip and are blocked by the material of the chip die itself or by the "leadframe," which refers to a stamped metal component with pins or formed leads at one end and connections to the chip die at the other end. Differences in leadframe shape details or attachments to pins or the die can help distinguish counterfeit components from genuine components.

SUMMARY

This disclosure provides a method, apparatus, and system to support the screening of electronic components for the detection of counterfeit articles.

In a first embodiment, a method includes selecting one or more analysis algorithms to be used to verify an authenticity of an electronic component. Each analysis algorithm identifies a type of data to be analyzed and/or a manner in which the data is to be collected. Each analysis algorithm also defines how the data is to be analyzed to verify the authenticity of the electronic component. The method also includes obtaining data associated with the electronic component. The method further includes analyzing the data associated with the electronic component using the one or more selected analysis algorithms to determine whether the electronic component is authentic. In addition, the method includes generating an output based on the analysis.

In a second embodiment, an apparatus includes at least one memory configured to store data associated with an electronic component. The apparatus also includes at least one processing device configured to select one or more analysis algorithms to be used to verify an authenticity of the electronic component. Each analysis algorithm identifies a type of data to be analyzed and/or a manner in which the data is to be collected. Each analysis algorithm also defines how the data is to be analyzed to verify the authenticity of the electronic component. The at least one processing device is also configured to analyze the data associated with the electronic component using the one or more selected analysis algorithms to determine whether the electronic component is authentic.

In a third embodiment, a non-transitory computer readable medium embodies a computer program. The computer program includes computer readable program code for selecting one or more analysis algorithms to be used to verify an authenticity of an electronic component. Each analysis algorithm identifies a type of data to be analyzed and/or a manner in which the data is to be collected. Each analysis algorithm also defines how the data is to be analyzed to verify the authenticity of the electronic component. The computer program also includes computer readable program code for obtaining data associated with the electronic component. The computer program further includes computer readable program code for analyzing the data associated with the electronic component using the one or more selected analysis algorithms to determine whether the electronic component is authentic. In addition, the computer program includes computer readable program code for generating an output based on the analysis.

In a fourth embodiment, a system includes handling equipment configured to position electronic components for inspection. The system also includes imaging equipment configured to obtain data associated with each electronic component. The system further includes scanning equipment configured to move the imaging equipment and/or the electronic components so that the imaging equipment is able to obtain the data associated with each electronic component. In addition, the system includes an analysis system configured to select one or more analysis algorithms to be used to verify an authenticity of the electronic components. Each analysis algorithm identifies a type of data to be analyzed and/or a manner in which the data is to be collected. Each analysis algorithm also defines how the data is to be analyzed to verify the authenticity of the electronic components. The analysis system is also configured to analyze the data associated with the electronic components using the one or more selected analysis algorithms to determine whether each of the electronic components is authentic.

Various implementations of these embodiments can provide a number of technical advantages. The specific technical advantage or advantages obtained can vary depending on the implementation. For example, conventional inspection systems are often able to perform an analysis of inspected components using a single predefined algorithm or a predefined set of algorithms and lack the ability to flexibly select one or more algorithms to be applied based on the data received. The embodiments described here support the flexible selection of algorithm(s) to be used to inspect electronic components. Among other things, this can allow multiple types of electronic components to be inspected using the inspection station. Moreover, the embodiments described here provide for faster inspections of electronic components and support repeatable processes that are not subject to human error. In addition, the embodiments described here can be used to inspect all or substantially all electronic components in a batch of products, which can help to increase confidence in the authenticity of the electronic components in the batch.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 11, described below, and the various embodiments used to describe the principles of the present invention in this patent document are by way of illustration only and should not be construed in any way to limit the scope of the invention. Those skilled in the art will understand that the principles of the present invention may be implemented in any type of suitably arranged device or system.

Figure 1:
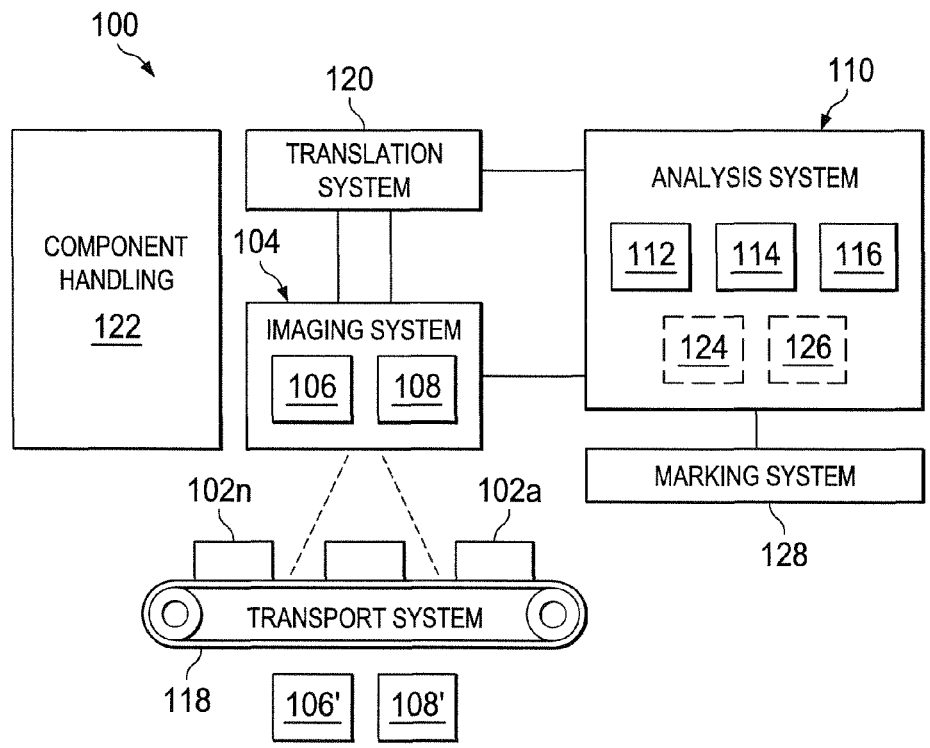
FIG. 1 illustrates an example inspection station for screening electronic components to detect counterfeit articles according to this disclosure.

FIG. 1 illustrates an example inspection station 100 for screening electronic components to detect counterfeit articles according to this disclosure. In this example, the inspection station 100 is used to inspect various electronic components 102a-102n and determine whether the electronic components 102a-102n are potentially counterfeit. The electronic components 102a-102n can denote any suitable components to be inspected, such as integrated circuit chips, other circuit components (such as resistors, capacitors, inductors, diodes, etc.), or integrated circuit chips or other circuit components mounted on structures. The components 102a-102n may be packaged in any of numerous ways that such components are delivered to end users. For example, the electronic components 102a-102n could be provided in a tray, on a tape and reel, sealed in blister packs or other packages, mounted on either side of a planar printed wiring board (PWB), or mounted on any surface of a three dimensional hybrid PWB assembly. In general, any components that could be used in electronic devices and that have one or more features capable of being used to distinguish between authentic and counterfeit articles can be inspected by the inspection station 100. Note that the electronic components 102a-102n in FIG. 1 could represent individual components or collections of components.

As shown in FIG. 1, the inspection station 100 includes an imaging system 104, which collects data regarding the electronic components 102a-102n being inspected. For example, the imaging system 104 could capture visual images, infrared images, X-ray wavelength data, and/or spectroscopic measurements of the electronic components 102a-102n. Any other or additional data could be collected by the imaging system 104. In some embodiments, when more than one imaging technique is utilized, the corresponding data sets can be overlayed and consolidated to create a combined multi-spectral dataset.

The imaging system 104 includes any suitable structure for capturing information about the appearance, structure, or composition of electronic components being inspected. In this example, the imaging system 104 includes at least one radiation source 106 and at least one radiation detector 108. As shown in FIG. 1, each radiation source 106 generates some form of radiation that is directed toward the electronic components 102a-102n. Example radiation sources 106 include visible, infrared, and ultraviolet light sources (such as light emitting diodes) and X-ray sources. A radiation source 106 may also be mounted at another location, such as below the electronic components 102a-102n at location 106'. Each radiation detector 108 detects radiation that has interacted with or that is generated by the electronic components 102a-102n. Example radiation detectors 108 include digital cameras, infrared detectors (including near-, short-wave, or long-wave detectors), X-ray sensors, and X-ray fluorescence (XRF) spectrometers. A radiation detector 108 may also be mounted at another location, such as below the electronic components 102a-102n at location 108'. In some embodiments, at least one radiation source 106 represents a homogenous and polarization-insensitive source that generates white light. Also, in some embodiments, at least one radiation detector 108 represents a high-magnification telecentric optical system.

In particular embodiments, one type of radiation could be directed at the electronic components 102a-102n, or multiple types of radiation could be directed at the electronic components 102a-102n. The type(s) of radiation could be selected based on various factors, such as the type of electronic component being inspected. Also, different types of radiation could be used at different times. For example, optical inspections could be performed for all electronic components 102a-102n using visible light, and X-ray or XRF inspections could be performed only for electronic components 102a-102n of questionable authenticity.

Any suitable image of an electronic component can be captured by the imaging system 104. For example, the imaging system 104 could capture instantaneous one-dimensional line scans, produce two-dimensional (2D) images, produce representations of three-dimensional (3D) surface features, or any combination thereof. Moreover, the imaging system 104 could generate data in any suitable manner, such as by combinations, comparisons, or mixing of wavelength-dispersed data, polarization data, or other optical or electronic representations of information associated with the optical physics contributing to an image (including results in transformational or reciprocal spaces, like Fourier or wavelet transforms). Additionally, digital filters (including digital filters matched to data characteristics requiring discrimination and analysis) could be used in the imaging system 104.

The data collected by the imaging system 104 is provided to an analysis system 110, which analyzes the data to determine whether the electronic components 102a-102n are potentially counterfeit. The analysis system 110 includes any suitable computing or processing system configured to analyze data associated with electronic components being inspected and determine whether the electronic components may be counterfeit. In this example, the analysis system 110 includes at least one processing device 112, at least one memory 114, and at least one communication interface 116. Each processing device 112 includes any suitable processing or computing device(s) configured to process information, such as a microprocessor, microcontroller, digital signal processor, field programmable gate array, application-specific integrated circuit, or other device(s). Each memory 114 includes any suitable storage and retrieval device(s), such as a volatile and/or non-volatile memory. Each communication interface 116 includes any suitable interface(s) configured to transmit or receive data, such as an Ethernet network interface or a radio frequency (RF) transceiver.

The inspection station 100 can further include or be associated with a transport system 118 and/or a translation system 120. The transport system 118 moves the electronic components 102a-102n into a suitable position for imaging by the imaging system 104. The transport system 118 includes any suitable structure for moving electronic components into an imaging position. Example types of transport systems 118 include one or more conveyor belts, tape and reel devices, movable trays, or robot pick and place devices. The type of transport system 118 used could vary depending on certain factors, such as whether the electronic components 102a-102n denote loose integrated circuit chips or printed circuit boards with connected integrated circuit chips.

The translation system 120 moves the imaging system 104 into a suitable position to measure one or more electronic components 102a-102n. For example, a large number of electronic components 102a-102n could be held in a tray. The translation system 120 could move the imaging system 104 along rows and columns of electronic components to allow scanning of the electronic components. The translation system 120 includes any suitable structure for moving an imaging system in order to image electronic components. One example type of translation system 120 is a gantry XYZ system.

Component handling equipment 122 can be provided to facilitate proper placement and positioning of the electronic components 102a-102n, such as on the transport system 118 or near the imaging system 104. For example, the component handling equipment 122 could include equipment for moving, correctly orienting, and positioning the electronic components 102a-102n being screened so that data about the electronic components 102a-102n can be collected correctly. Any suitable component handling equipment 122 could be used here, such as robotic equipment.

Counterfeit electronic components routinely include one or more detectable attributes. For example, integrated circuit chips routinely include markings such as manufacturer logos, part numbers, date codes, lot codes, and "pin 1" dimple marks on tops or bottoms of the chips. Differences in date or lot codes, fonts, letter sizes, letter spacings, or logos can be indicative of counterfeit items. Also, markings may be laser etched into authentic products and printed (such as via ink jet printers) onto counterfeit products, so differences in spectral reflectivity or "splotchiness" of markings can be indicative of counterfeit items. Further, spatial displacement of logos or other markings can be indicative of counterfeit items. Other attributes that may be indicative of counterfeiting include the finish, reflectivity, and flatness (or irregularity in flatness) of the top surfaces of integrated circuit chips, the dimensions of the overall chips, the height of molded portions of the chips, and the edge straightness of molded portions of the chips. Still other attributes that may be indicative of counterfeiting include the count, style, geometry, symmetry, and flatness of solder leads.

Any of these or other features (or any combination thereof) can be analyzed by the analysis system 110 in order to detect potentially counterfeit products. In FIG. 1, the analysis system 110 supports various analysis algorithms 124 that can be stored in the at least one memory 114 and executed by the at least one processing device 112. Each analysis algorithm 124 could define both (i) the types of data to be analyzed by the inspection station 100 and/or the manner in which the data is to be collected by the inspection station 100 and (ii) the analysis routine(s) to be applied to the data collected by the inspection station 100. The algorithms 124 can be optimized to detect various attributes that are indicative of potential counterfeiting. The optimizations can include, for instance, those for maximum throughput, highest accuracy, highest or lowest false accept rate, or other processing criteria.

The analysis system 110 also supports a flexible selection algorithm 126, which (as described below) can be used to automatically select the algorithm(s) 124 employed. The flexible selection algorithm 126 could, for example, select one or more algorithms 124 based on preliminary measurements of one or more attributes of the components 102a-102n. This allows the inspection station 100 to vary both the types of data collected/manner in which the data is collected and the analysis of that data.

The specific analysis algorithms 124 selected and executed by the analysis system 110 could vary depending on various factors, such as the type(s) of data available from the imaging system 104. For example, when visual images are provided, algorithms 124 can be executed to detect evidence of re-marking, blacktopping, or other tampering with the electronic components 102a-102n. When X-ray scans are provided, algorithms 124 can be executed to detect and verify the internal construction of the electronic components 102a-102n. When XRF spectrographic measurements are provided, algorithms 124 can be executed to detect and verify the elemental constituents of the electronic components 102a-102n. The analysis algorithms 124 executed by the analysis system 110 could also vary based on the electronic components 102a-102n being inspected.

As noted here, the analysis system 110 supports a two-level approach to inspecting the electronic components 102a-102n. In the first level, an initial algorithm (the flexible selection algorithm 126) executed by the analysis system 110 identifies the type of component being inspected or other information and selects one or more second-level algorithms (one or more algorithms 124) based on that information. In the second level, the analysis system 110 uses the selected algorithm(s) 124 to analyze the electronic components and make a determination whether each electronic component is potentially counterfeit. Various types of second-level algorithms can be supported, such as algorithms designed to comply with different industry standards for detecting counterfeit parts (like the AS5556 or IDEA-STD-1010 standards).

The analysis algorithms 124 executed by the analysis system 110 could vary based on any other factors. Other factors could include the positioning accuracy requirements of the electronic components 102a-102n, the image capture speed or field of view of an imaging device used to image the electronic components 102a-102n, and the packaging of the electronic components 102a-102n (or lack thereof). For instance, different algorithms 124 could be used depending on whether integrated circuit chips are loose or soldered to printed circuit boards.

Depending on the algorithms 124 selected, the analysis system 110 could detect counterfeit electronic components with or without reference to a "golden" or "reference" component (a known good/authentic component). For example, once the type of electronic component being inspected is identified, the analysis system 110 could access a database of records to identify one or more expected characteristics of that type of electronic component. The expected characteristics could be based on one or more characteristics of at least one known good component, historical data associated with multiple lots of known good components, or any other suitable data. Differences between the measured characteristic(s) of the electronic components 102a-102n and the expected characteristic(s) could be indicative of counterfeiting. The analysis system 110 could also or alternatively measure and compare one or more characteristics of the electronic components 102a-102n themselves, such as to identify the variability of the characteristic(s) within a single lot of the electronic components 102a-102n. Excessive variations in the measured characteristic(s) of the electronic components 102a-102n could again be indicative of counterfeiting.

In this way, the inspection station 100 can be used to provide rapid throughput for the screening of all or substantially all components in a lot, which can be accomplished with little or no human intervention in the inspection process. The inspection station 100 also enables non-destructive screening for specific counterfeit methods that are traditionally only found through destructive screening methods. Inspections can be conducted per appropriate industry standards for counterfeit parts, and multiple analyses (even those involving different spectrums of radiation) could be performed for each individual electronic component at the same time. Algorithms can be customized to detect evidence of specific counterfeiting techniques, and algorithms can be automatically updated or introduced during processing to deal with variations, changes, or improvements in counterfeiting techniques. In addition, the inspection station 100 can detect counterfeit electronic components more rapidly, which enables the testing of every single electronic component for counterfeiting (rather than a very small subset of the electronic components). Additional details regarding example implementations and operations of the inspection station 100 are provided below.

Note that each algorithm here can be implemented in any suitable manner, such as via computational or physical mechanisms. For instance, an algorithm could be implemented via software/firmware instructions or via hardware logic. Also, the automatic selection of algorithms can involve the selection of a computational algorithm and/or the selection of hardware, physical operations, subsequent flexible algorithmic processing, and pass/fail determinations. For example, based on an irregularity in font shape, the algorithm 126 might select a path that tells the inspection station 100 to do an inspection for leadwire bonding irregularities.

In addition, note that the inspection station 100 described here could find use in a number of environments. For example, the inspection station 100 could be used as part of a "final gate" component acceptance process at electronic assembly houses, brokers, distributors, and test houses. Specific industries where this functionality might be particularly useful include the defense industry (where counterfeit products raise reliability concerns of military hardware) and the medical and energy industries (where counterfeit products raise significant concerns for liability or patient harm).

To support the identification of electronic components 102a-102n that are determined to be potentially counterfeit, a marking system 128 can be provided in the inspection station 100. The marking system 128 could be used to create a visible or other marking on an electronic component determined to be potentially counterfeit. Any suitable mechanism can be used to create a visible or other marking on an electronic component.

Although FIG. 1 illustrates one example of an inspection station 100 for screening electronic components to detect counterfeit articles, various changes may be made to FIG. 1. For example, various components in FIG. 1 could be combined, subdivided, rearranged, or omitted or additional components could be added according to particular needs. As a specific example, the functionality of the imaging system 104 and the analysis system 110 could be combined.

Figure 2:
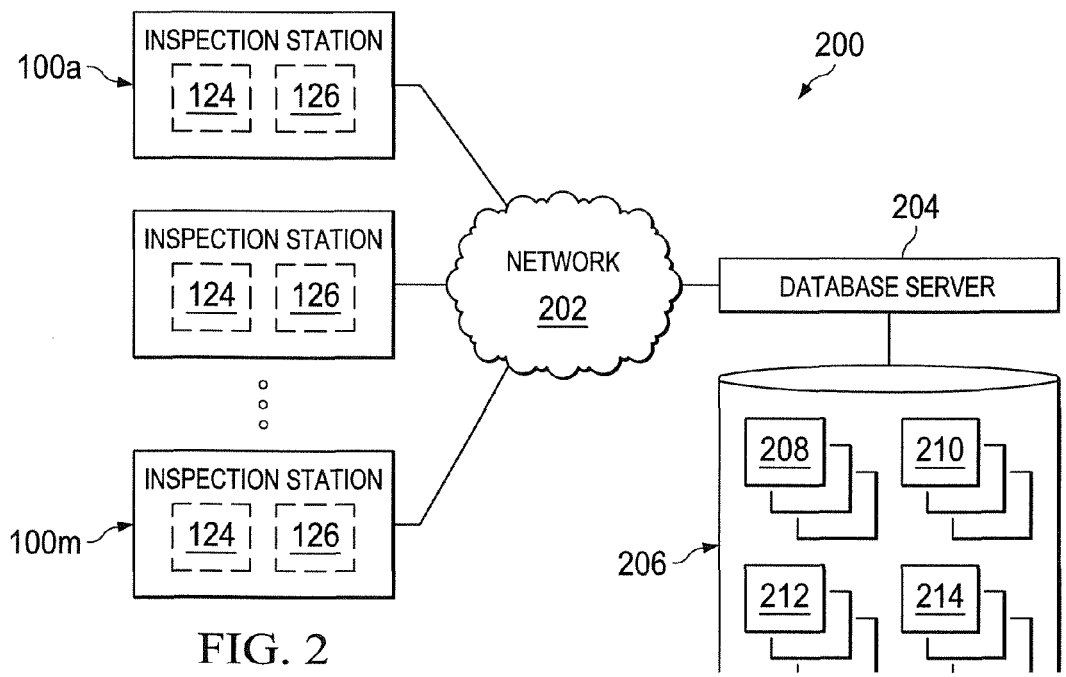
FIG. 2 illustrates an example system for screening electronic components to detect counterfeit articles according to this disclosure.

FIG. 2 illustrates an example system 200 for screening electronic components to detect counterfeit articles according to this disclosure. As shown in FIG. 2, the system 200 includes multiple inspection stations 100a-100m, each of which could be the same as or similar to the inspection station 100 shown in FIG. 1 and described above. The inspection stations 100a-100m here could be used at a single location or at multiple locations (and possibly separated by large distances).

The system 200 also includes a network 202. The network 202 facilitates communication between various components coupled to the network 202. For example, the network 202 may communicate Internet Protocol (IP) packets, frame relay frames, Asynchronous Transfer Mode (ATM) cells, or other suitable information between network addresses. The network 202 may include one or more local area networks, metropolitan area networks, wide area networks, all or a portion of a global network, or any other communication system(s) at one or more locations.

A database server 204 is coupled to the network 202 and controls access to and use of a database 206, which stores various information used by the inspection stations 100a-100m. For example, the database 206 could store data records 208 identifying the characteristics of different "golden" or reference electronic components. These characteristics define the expected characteristics of electronic components and can be compared to measured characteristics of electronic components 102a-102n to identify potential counterfeiting. The characteristics in the data records 208 could be identified in any suitable manner, such as by testing known good lots of electronic components or by obtaining information about manufacturing capabilities or tolerance thresholds of electronic component manufacturers.

The database 206 could also store data records 210 identifying permissible product-to-product variations within a single lot of electronic components. If components in a single lot exhibit variations above the permissible levels, this can be used to identify potential counterfeiting. Again, the information in the data records 210 could be obtained in any suitable manner, such as by testing known good lots of electronic components, by using information about manufacturing capabilities or tolerance thresholds of electronic component manufacturers, or by testing lots of unknown-quality components for variations of key characteristics within the lot.

The database 208 could further store algorithms 210, which can be distributed to the inspection stations 100a-100m as the algorithms 124 and/or 126. An inspection station 100a-100m could request one or more algorithms 210 during startup, in response to identifying a particular type of electronic component being tested, at specified intervals, or in any other suitable manner. Among other things, this allows updated or new algorithms 210 to be easily provided to the inspection stations 100a-100m. The database 208, independently or in coordination with other computing assets attached to the network 202, can provide guidance or updates to the flexible selection algorithm 126 in each inspection station 100a-100n that guide selection of which algorithms are selected and applied to items undergoing inspection. In addition, the database 208 could store historical inspection data records 214, which identify the results of various scans of electronic components.

The use of a central database 206 could provide various benefits depending on the implementation. For example, information from multiple inspection stations 100a-100m could be collected by the database server 204 and distilled for storage in the database 206. This information could include the results of inspections for numerous electronic components, and the inspection data could be sorted and used to perform various tasks. One task could include updating the data records 208-210 to reflect improved measurements of characteristics of known good products or improved measurements of variability in known good product lots. This can help to provide an intelligent update or learning feature for the inspection stations.

In some embodiments, the database 206 can act as a single point of reference for all inspection stations. The database 206 can also serve as an ever-evolving tool that sorts and files authentic versus counterfeit historic inspection data, a catalog for manually troubleshooting questionable parts, and a catalog of "golden standard" references of inspection values or variation in values for each component or component feature.

Although FIG. 2 illustrates one example of a system 200 for screening electronic components to detect counterfeit articles, various changes may be made to FIG. 2. For example, the system 200 could include any number of inspection stations, networks, servers, and databases. Also, an inspection station could be configured to operate in a stand-alone manner without reference to the contents of a central database 206.

Figure 3:
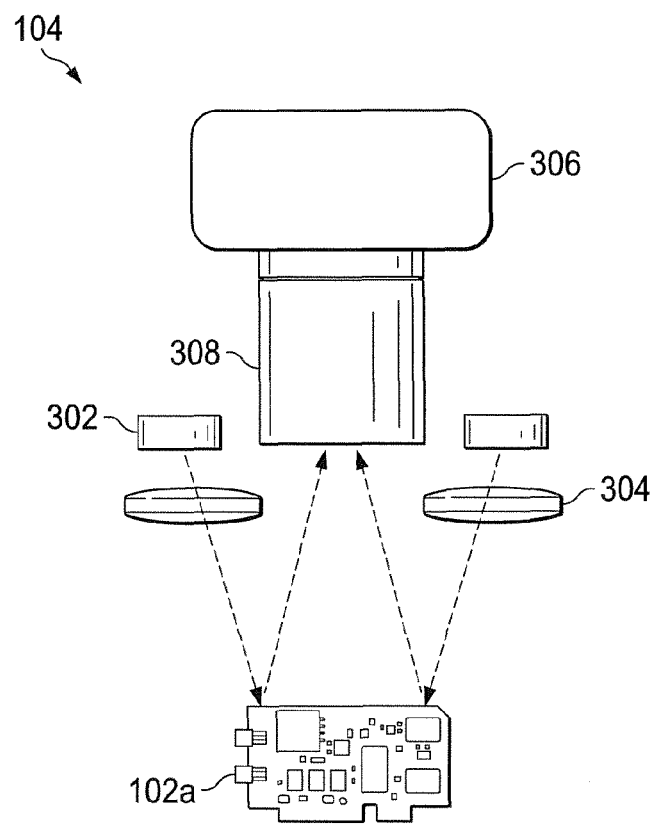
FIGS. 3 and 4 illustrate example electronic component scanning mechanisms for an inspection station according to this disclosure.
Figure 4:
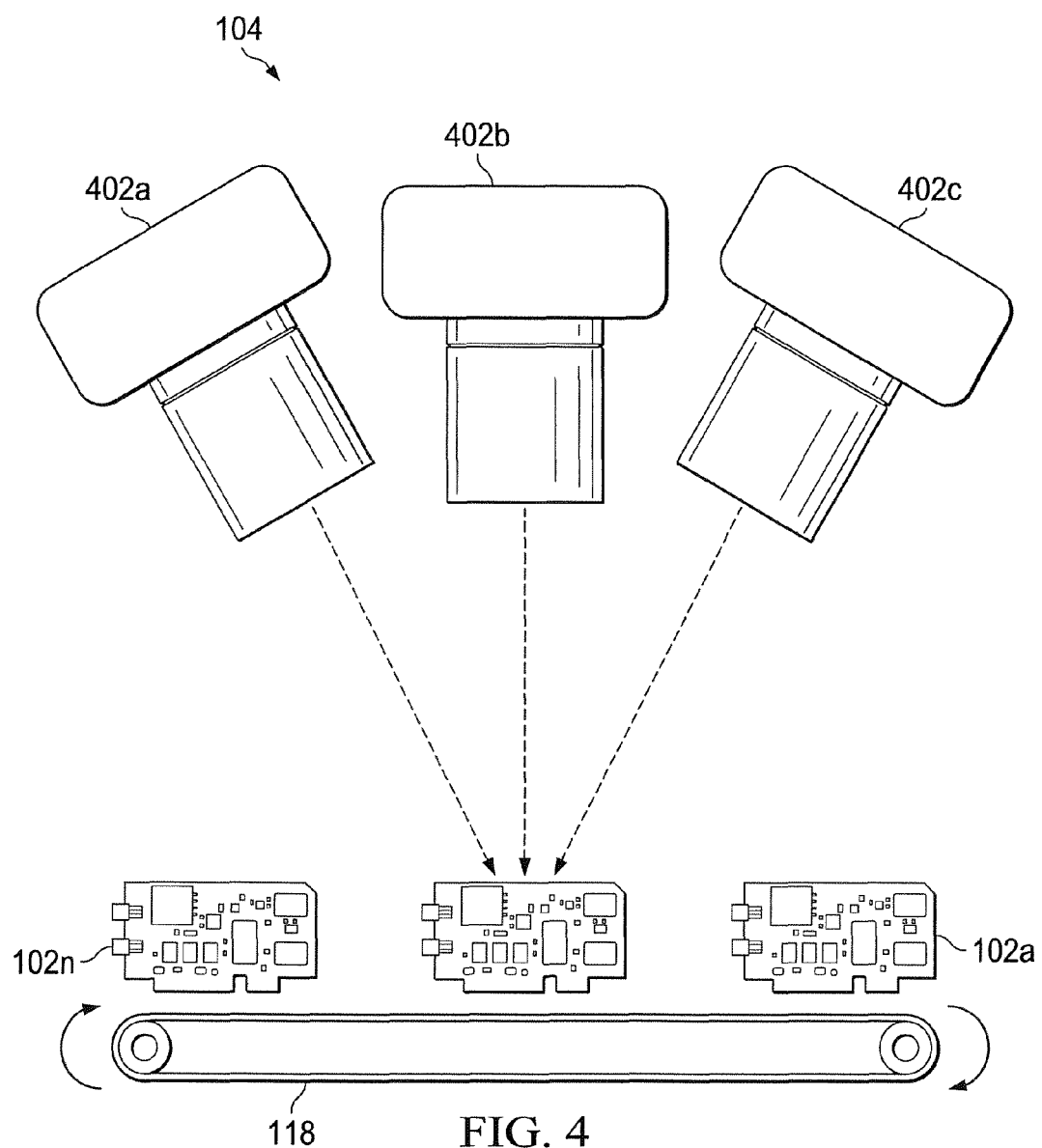

FIGS. 3 and 4 illustrate example electronic component scanning mechanisms for an inspection station according to this disclosure. More specifically, FIGS. 3 and 4 illustrate example implementations of the imaging system 104 in the inspection station 100 of FIG. 1. As shown in FIG. 3, one implementation of the imaging system 104 uses a ring light 302, which denotes one or more illumination devices (such as one or more light emitting diodes) arranged in a circular pattern or other pattern to illuminate an electronic component 102a from multiple directions. At least one linear polarizer 304 polarizes the generated light. Light reflecting off the electronic component 102a is captured using an imager 306, such as a digital camera, which includes a lens system 308 for focusing the light. Although not shown, the imager 306 may include another linear polarizer, which could be at a 90° orientation with respect to the polarizer 304, to help improve the image fidelity (brightness and contrast) of images captured by the imaging system 104.

In some embodiments, the ring light 302 represents a bright-field illuminator that generates white light. The size, location, angulation of beam axis, and divergence of the ring light 302 may be known, which helps during image processing. Bright-field illumination can be used to generate evenly illuminated, high brightness, high contrast images. Also, in some embodiments, the imager 306 represents a telecentric finite conjugate machine vision imaging optic, such as a high-magnification telecentric digital microscope, that automatically takes high fidelity photographs of all electronic components in a lot under inspection. The use of a telecentric imaging optic can help to maintain constant magnification and image size regardless of the depth of a focused feature, reducing errors caused by potential defocus. The imager 306 can have a certain degree of magnification combined with a high-resolution focal plane array (FPA) detector for high-fidelity imaging. The frame rate of the imager 306 can be fast enough to capture one or more images of every component being inspected, where the needed speed of the imager 306 is based (at least in part) on the speed of the transport system 118 and/or the translation system 120 and the desired inspection time.

Note that FIG. 3 illustrates the use of a single imager 306 to capture information about an electronic component being inspected. As shown in FIG. 4, multiple imagers 402a-402c could also be used to capture information about an electronic component being inspected. Illumination sources are omitted here for clarity. The imagers 402a-402c could represent visible-light cameras that capture images of the electronic component being inspected from multiple angles. The imagers 402a-402c could also denote different types of detectors (such as visible, infrared, X-ray, or spectroscopic detectors) that support different types of analyses. Any combination of imagers could be used in the imaging system 104. In FIG. 4, the transport system 118 is implemented using a conveyor belt. This is for illustration only, and any other suitable type(s) of transport system(s) could be used to move electronic components. Additionally, the components 102a-102n in FIGS. 3 and 4 can represent a plurality of components, such as trays of integrated circuits, that are imaged substantially simultaneously, such as by using a single imager or imager array.

Although FIGS. 3 and 4 illustrate examples of electronic component scanning mechanisms for an inspection station, various changes may be made to FIGS. 3 and 4. For example, an inspection station could include any suitable detector(s) in any suitable arrangement(s) for capturing information about one or more electronic components under inspection.

Figure 7:
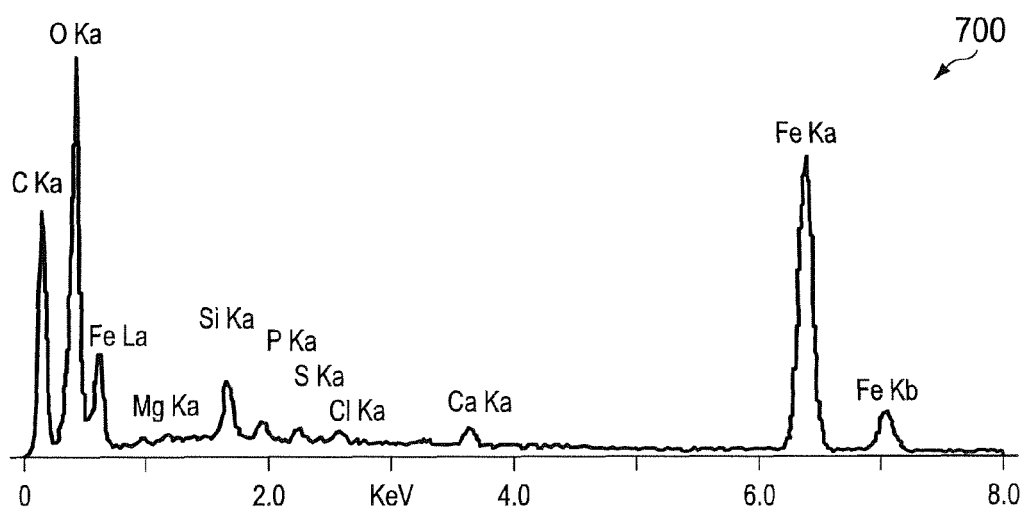
FIGS. 5 through 7 illustrate example data collected by an inspection station according to this disclosure.
Figure 5:
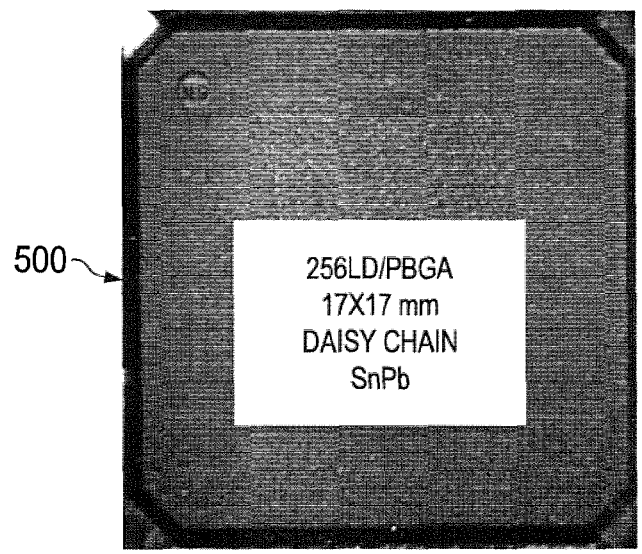
Figure 6:
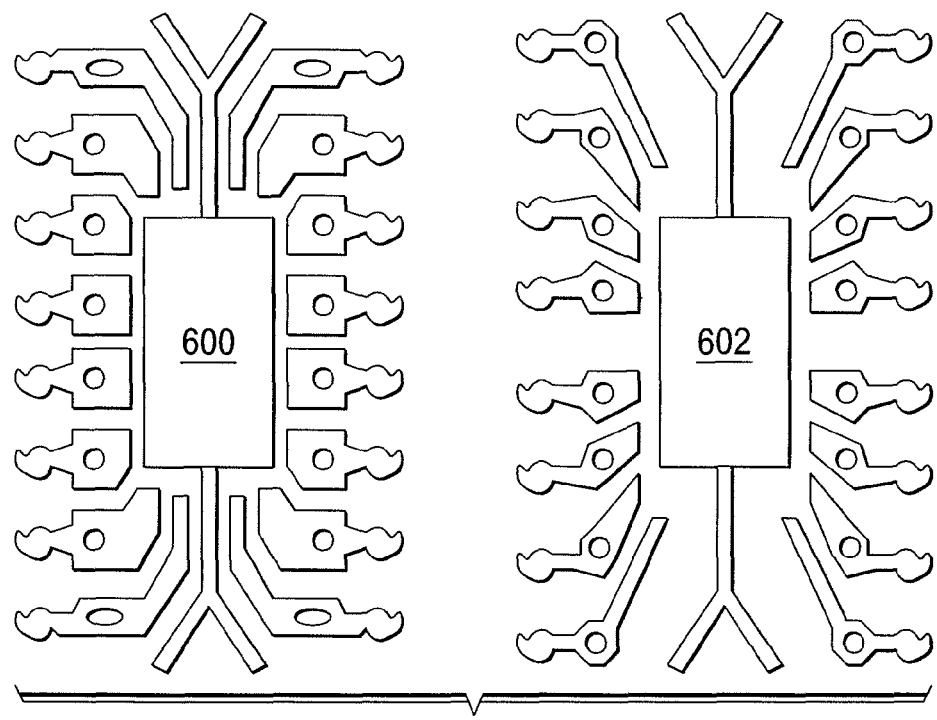

FIGS. 5 through 7 illustrate example data collected by an inspection station according to this disclosure. FIG. 5 illustrates an example visible-light image 500 of an electronic component under test. As shown in FIG. 5, the image 500 captures an integrated circuit chip, along with one or more of the chip's associated leads. The image 500 also captures text printed or engraved onto the chip (possibly including a logo of the chip's manufacturer not shown here) and a "pin 1" dimple in the upper left corner of the chip. As described below, any of these features or any combination of these features can be analyzed to determine whether the integrated circuit chip captured in the image 500 is authentic or counterfeit.

FIG. 6 illustrates example low-power X-ray scans 600-602 of different integrated circuit chips. As can be seen here, the scans 600-602 indicate that the integrated circuit chips have different metallic structures inside the chips. The X-ray scan of a chip can therefore be compared (either to a known good component or another component in the same lot or to the typical variation from chip to chip) to determine whether counterfeiting is suspected.

FIG. 7 illustrates an example XRF spectrographic plot 700 identifying the elemental composition of an integrated circuit chip. As can be seen here, the plot 700 contains various spikes having different amplitudes in different locations. The spikes and their amplitudes identify the composition of an integrated circuit chip. Comparing different plots for different integrated circuit chips can help to identify whether the different integrated circuit chips have the same/similar elemental composition.

Data such as that shown in FIGS. 5 through 7 could be generated by the imaging system 104 and provided to the analysis system 110. The analysis system 110 could analyze this data, such as via comparisons with data for reference components or comparisons to components within the same lot, to identify potentially counterfeit items.

Although FIGS. 5 through 7 illustrate examples of data collected by an inspection station, various changes may be made to FIGS. 5 through 7. For example, the image, X-ray scans, and XRF spectrographic plots shown here are examples only, and other electronic components would have their own images, X-ray scans, and XRF spectrographic plots. Also, other or additional types of data could be generated by the imaging system 104 and analyzed by the analysis system 110.

Figure 8:
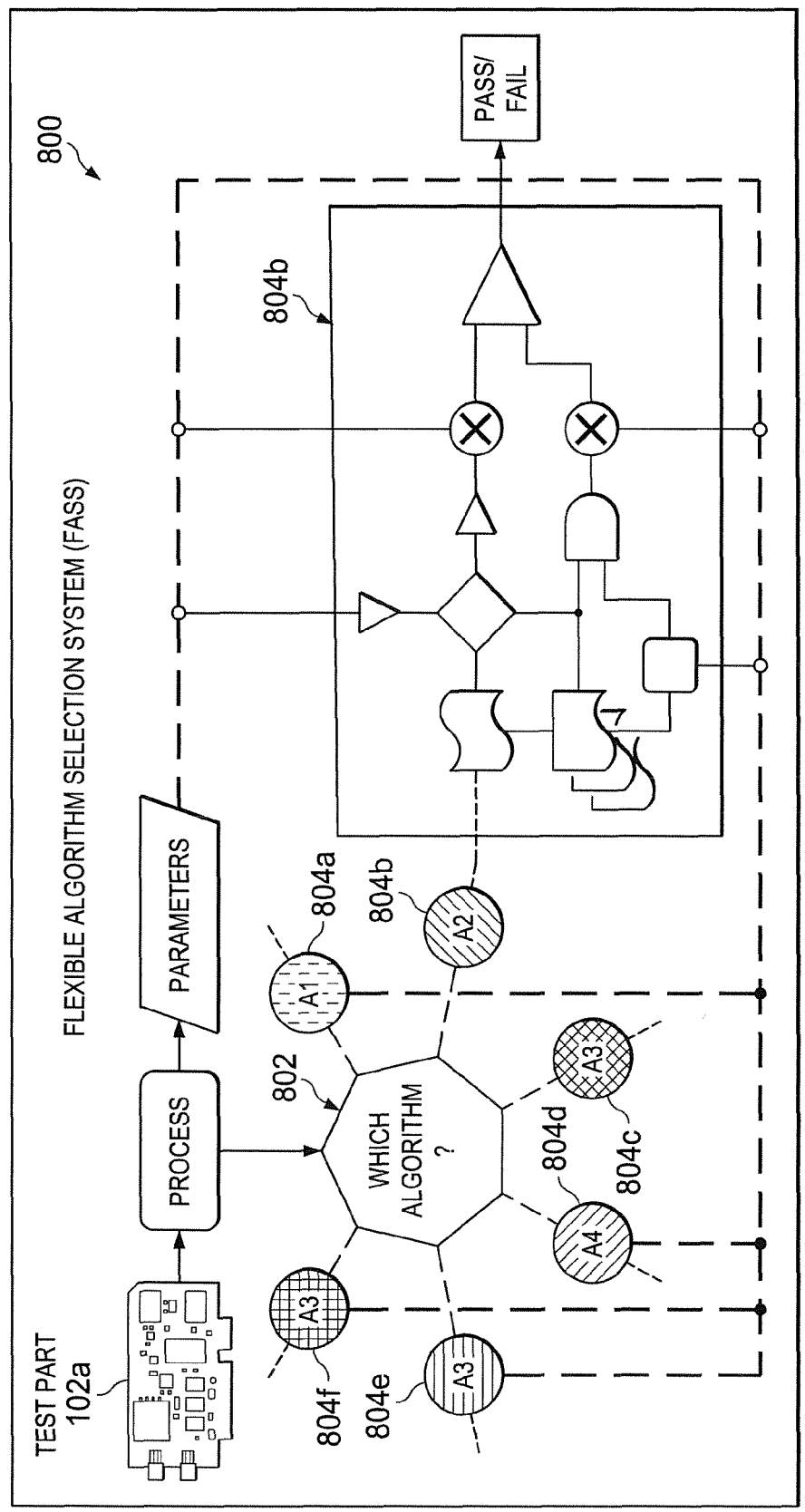
FIG. 8 illustrates an example flexible algorithm selection technique for selecting one or more algorithms to be used for screening electronic components according to this disclosure.

FIG. 8 illustrates an example flexible algorithm selection technique 800 for selecting one or more algorithms to be used for screening electronic components according to this disclosure. The technique 800 could, for example, be implemented by the analysis system 110 to select and execute the appropriate algorithm(s) for analyzing data about one or more electronic components 102a-102n being inspected.

As shown in FIG. 8, the flexible algorithm selection technique 800 includes a "level one" algorithm 802 and various "level two" algorithms 804a-804f. The "level one" algorithm 802 performs an initial analysis of data associated with an electronic component 102a and determines which "level two" algorithm(s) 804a-804f will be used during the inspection of that electronic component 102a.

As an example, the "level one" algorithm 802 could analyze an image of the electronic component 102a and identify a manufacturer and part number of the electronic component 102a. The appropriate "level two" algorithm(s) 804a-804f for that type of electronic component could then be selected. As another example, the "level one" algorithm 802 could analyze an image of the electronic component 102a and compare the image to images of various reference components. The similarity of the image of the electronic component 102a to different reference component images can be ranked, and a determination can be made which reference component or components most closely match the image of the electronic component 102a. The appropriate "level two" algorithm(s) 804a-804f associated with the reference component(s) can then be automatically selected. The detailed determination of which reference component or components most closely match the electronic component 102a could occur in any suitable manner. For instance, the size, shape, pin layout, and other characteristics of the electronic component 102a could be compared against the sizes, shapes, pin layouts, and other characteristics of the reference components to select which reference components are most similar to the electronic component 102a.

Note that the identification of at least one reference component need not occur in order to select one or more of the "level two" algorithms 804a-804f. For example, the database 206 may lack data records 208 identifying characteristics of known good lots of the same type of electronic component 102a or information about the manufacturing capabilities or tolerance thresholds of the manufacturer of the electronic component 102a. In that case, the "level one" algorithm 802 could select one or more "level two" algorithms related to measuring the variability of any suitable characteristic(s) of multiple electronic components within the same lot, without reference to any known good reference components or any manufacturing capabilities or tolerance thresholds of a manufacturer.

The selected "level two" algorithms 804a-804f identify the types of data to be analyzed by the inspection station 100 and/or the manner in which the data is to be collected by the inspection station 100, as well as the analysis technique(s) for analyzing the data associated with the electronic component 102a, in order to determine whether the electronic component 102a is counterfeit. For example, the "level two" algorithms 804a-804f could indicate whether optical images, infrared or X-ray scans, or XRF measurements are used. The "level two" algorithms 804a-804f could also analyze logos, images, text, pin dimples, and other characteristics of the electronic component. In particular embodiments, the "level two" algorithms 804a-804f could analyze the following characteristics of the electronic component under inspection:

the size of electronic component;
the location of the "pin 1" marker on the electronic component;
the dimple size of the "pin 1" marker on the electronic component;
the size of text characters on the electronic component;
the font of text characters on the electronic component;
the spacing between text characters on the electronic component;
the position of text characters on the electronic component with respect to a known location (such as the "pin 1" location);
the straightness or perpendicularity of mold lines; and
the surface finish or roughness of molded surfaces.

For example, the "level two" algorithms 804a-804f can perform pattern matching using the logo on the electronic component to known good logos of the same manufacturer. In addition, the "level two" algorithms 804a-804f could analyze the following characteristics of the electronic component under inspection (assuming the electronic component can be flipped):

the uniformity of solder plating on the electronic component;
the uniformity of interfaces of solder interconnects to the body of the electronic component;
the flatness of the solder leads on the electronic component; and
the quality of lead ends of the electronic component.

Any single one of these features or any combination of these features could be analyzed using specified "level two" algorithms 804a-804f to determine whether the electronic component 102a is counterfeit. As noted above, the specific algorithms selected could be based on the type of electronic component, the positioning accuracy requirements of the electronic component, the image capture speed or field of view of any imaging device used to image the electronic component, and the packaging of the electronic component.

In this way, the technique 800 supports a suite of image processing algorithms 124 to perform comparative analysis of various features that uniquely distinguish authentic and counterfeit components. The algorithms 804a-804f provide results in the form of pass/fail indicators, which indicate whether counterfeiting is suspected for a single component or a group of components. The overall pass/fail indicator for a component could be based on statistical variances within a lot (without use of a reference part), a comparison of the component's characteristic(s) to one or more reference parts, or a comparison of the component's characteristic(s) to dimensions or tolerances of manufacturer. The inspection station 100 could use the marking system 128 to mark or otherwise identify counterfeit components. The suite of algorithms used here provides a robust blend of target discriminators that distinguish between authentic and counterfeit components based on particular features that represent potential signatures evidencing counterfeiting.

In some embodiments, different features could be weighted differently during the analysis of an electronic component when generating a pass/fail indicator. For example, statistical weightings could be used across all features of interest, and the weights could vary. As a particular example, features that are easier to counterfeit may be given less weight since similarity between authentic and counterfeit components is easier to achieve. In contrast, features that are harder to counterfeit may be given more weight since similarity between authentic and counterfeit components is harder to achieve.

Mathematically, this approach can be represented as a weighted partial least squares (wPLS) problem, where the weights on the inputs are determined by criteria such as historical variation in the accuracy with which the input parameters may be determined. In this formalism, the number of weighted inputs is generally much larger than the number of outputs, and component acceptability is determined by comparison to a metric for each output variable.

Also, in some embodiments, a confidence level can be associated with a pass/fail indicator. The confidence level can identify how confident the analysis system 110 is in its determination that a component is or is not counterfeit. The confidence level could be calculated in any suitable manner. For example, the confidence level could be based on the size of the lot of components being inspected, where inspections of larger lots may lead to higher confidence levels. The confidence level could also be based on the number of "golden" or reference components used in an inspection, where inspections made with reference to more reference components may lead to higher confidence levels.

Note that before placing an inspection station 100 into use, the inspection station 100 can be calibrated and trained. Calibration of an inspection station 100 can involve identifying current illumination, image capture, or other features of the inspection station 100. For example, one or more known calibration tiles or other objects could be illuminated by the inspection station 100, and one or more images or other data associated with the calibration tiles or other objects could be analyzed. Based on the analysis results, changes could be made to the illumination or image capture mechanisms, correction factors could be applied to calculations performed by the inspection station 100, or other actions could occur so that the determined characteristics of the calibration tiles or other objects match the known characteristics of the calibration tiles or other objects. However, any other suitable technique could be used to calibrate an inspection station 100.

Training of the inspection station 100 generally refers to the identification of information to be used when analyzing a component being inspected. For example, the training could include identifying a "signature" of known good reference components. In some circumstances, a known good signature can be obtained by scanning known good components with a calibrated inspection station 100. The signature could be uploaded to the database 206 for later use or for use by other inspection stations 100. The training could be controlled by a software program executed by the inspection station 100, where the software program automatically controls the number of requisite "good" reference samples and test orientations and subsequently defines the limits of acceptance. Note, however, that training may not be necessary or may be minimized if a known good signature can be obtained, such as from the database 206.

Although FIG. 8 illustrates one example of a flexible algorithm selection technique 800 for selecting one or more algorithms to be used for screening electronic components, various changes may be made to FIG. 8. For example, any number of "level one" and "level two" algorithms could be supported. Also, additional levels of algorithms could also be supported. For instance, a third level of algorithms could be used to more thoroughly test electronic components that fail the level two tests or that are on the border of failing the level two tests. The "level three" algorithms could involve more detailed analyses or analyses in different spectrums, such as X-ray or XRF analyses. Further, the deterministic automated selection of algorithms can be calibrated and trained as described above.

Figure 9:
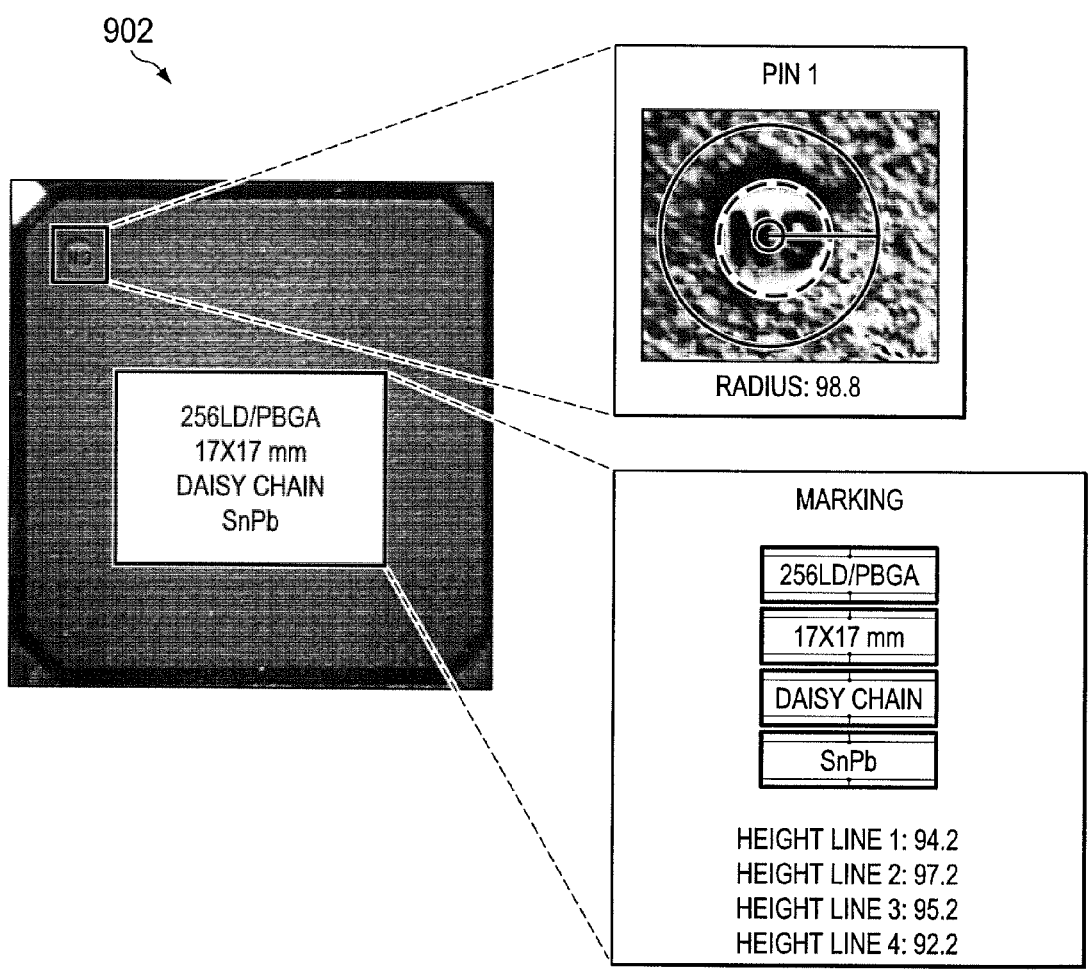
FIGS. 9 and 10 illustrate example analysis results associated with electronic components according to this disclosure.
Figure 10:
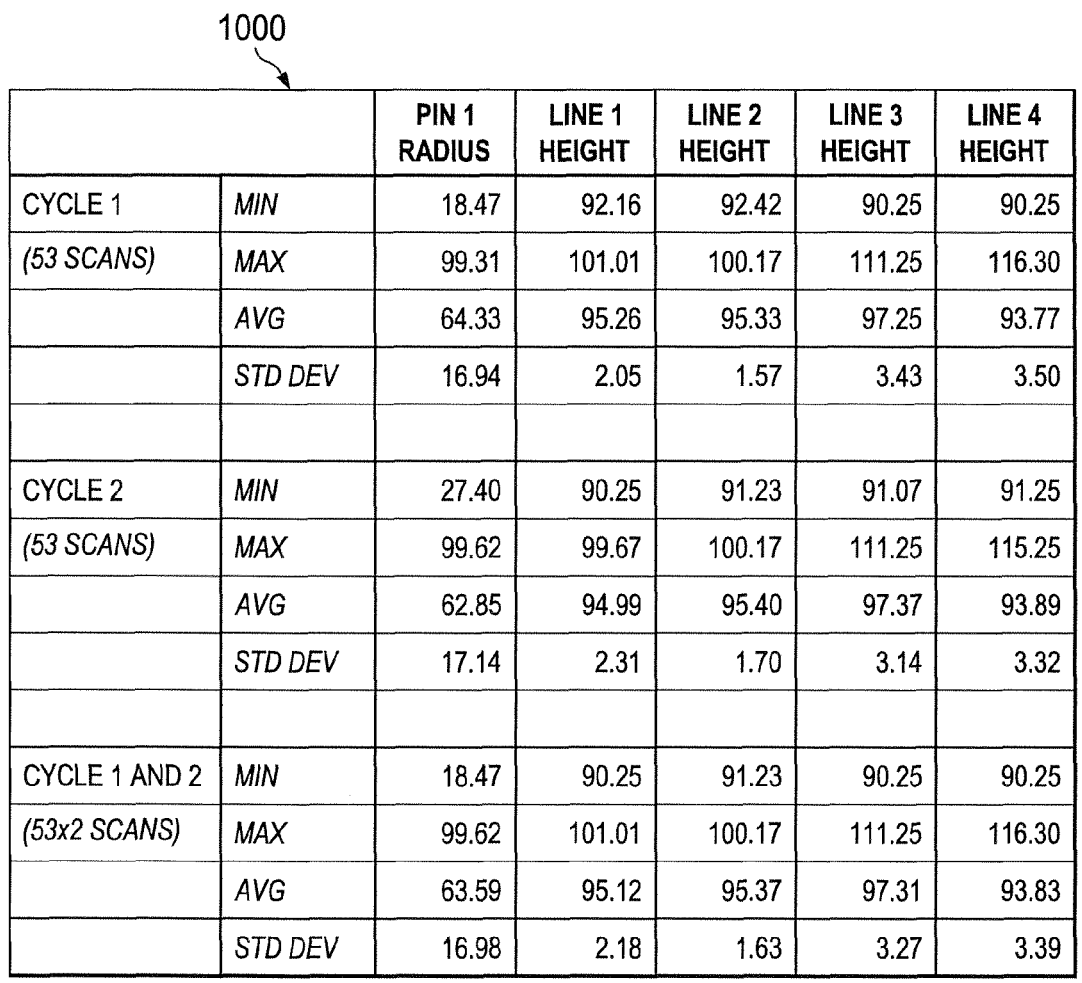

FIGS. 9 and 10 illustrate example analysis results associated with electronic components according to this disclosure. In FIG. 9, an image 902 of a component is analyzed to identify the radius of a "pin 1" marker and a height of various text on the component. The characteristics of counterfeit components can differ significantly from the characteristics of authentic components, allowing the inspection station 100 to identify the counterfeit item.

In FIG. 10, an example report 1000 contains analysis results for multiple electronic components. The report 1000 summarizes analysis results, such as those shown in FIG. 9, for easy review. In this example, the analysis system 110 has measured the "pin 1" radius and the heights of four lines of text on various electronic components. As can be seen here, there are significant variations in the measured values. Even without reference to any known good components, the inspection station 100 could flag a subset or all of these electronic components as being counterfeit.

Although FIGS. 9 and 10 illustrate examples of analysis results associated with electronic components, various changes may be made to FIGS. 9 and 10. For example, analysis results generated by an inspection station 100 could be used in any other suitable manner. As a particular example, analysis results could be uploaded to the database 206 for storage and later use.

Figure 11:
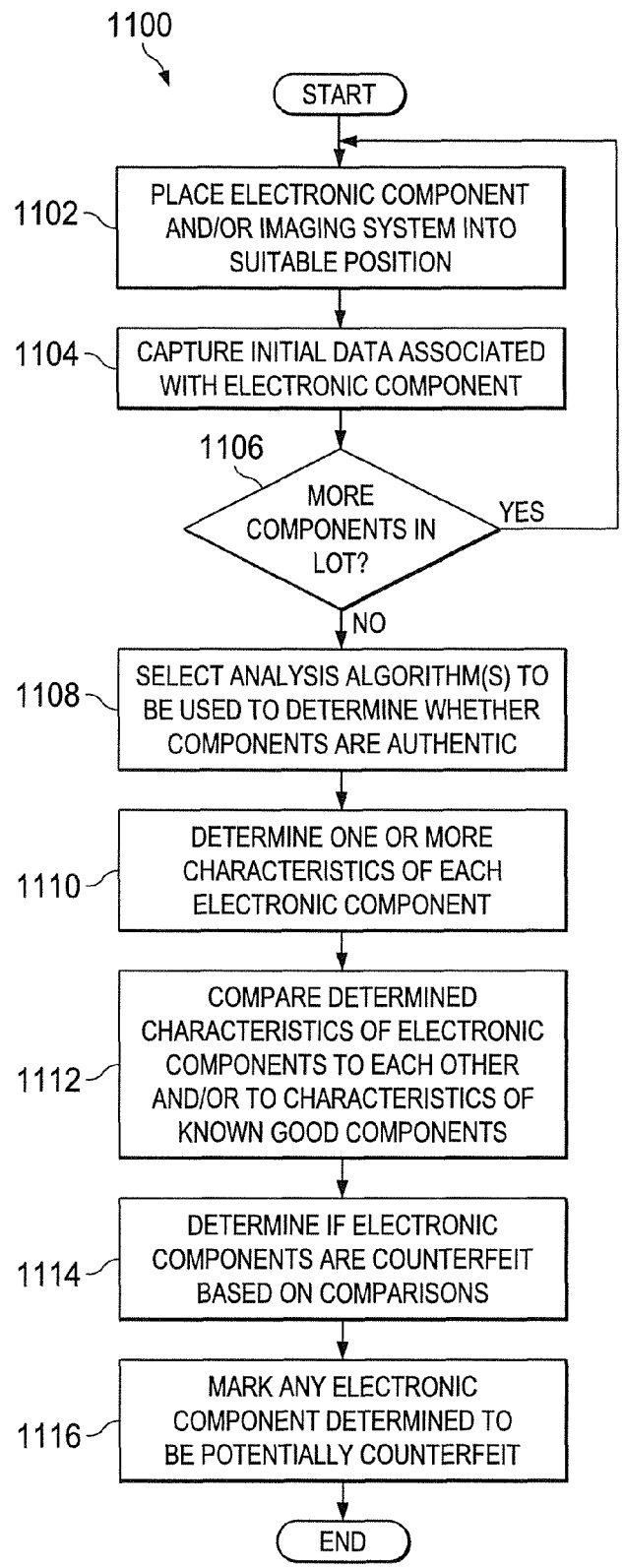
FIG. 11 illustrates an example method for screening electronic components to detect counterfeit articles according to this disclosure.

FIG. 11 illustrates an example method 1100 for screening electronic components to detect counterfeit articles according to this disclosure. For ease of explanation, the method 1100 is described with respect to the inspection station 100 of FIG. 1 operating in the system 200 of FIG. 2. However, the method 1100 could be used by any suitable device and in any suitable system.

As shown in FIG. 11, an electronic component or an imaging system is placed into a suitable position at step 1102, and initial data associated with the electronic component is captured at step 1104. This could include, for example, placing the electronic component into a suitable position using the transport system 118 or moving the imaging system 104 using the translation system 120. The imaging system 104 could capture any suitable data associated with the electronic component, such as one or more images, X-ray scans, or XRF spectrographic measurements. A determination is made whether there are more electronic components in a lot to be imaged at step 1106. If so, the process returns to step 1102 to position and capture data associated with another electronic component.

One or more analysis algorithms to be used to determine whether the components are authentic are selected at step 1108. This could include, for example, the analysis system 110 using the flexible selection algorithm 126 to make an initial determination of which analysis algorithms 124 are to be used. As a particular example, the analysis system 110 could analyze the initial data from the imaging system 104 to identify the type of part being inspected and then select the appropriate algorithm(s) 124 for that part.

One or more characteristics of each electronic component are identified at step 1110. This could include, for example, the analysis system 110 analyzing the images, X-ray scans, or XRF spectrographic measurements to identify various characteristics of each electronic component. Example characteristics could include any individual feature or combination of features described above. Note that this step could include analyzing the initial data collected during step 1102 or collecting additional data about each electronic component. For instance, an optical image of an electronic component could be used to select the analysis algorithm(s), and additional data as defined by the analysis algorithm(s) could then be obtained and analyzed to identify the characteristic(s) of each electronic component.

The determined characteristics of the electronic components are compared to one another or to characteristics of one or more known good components at step 1112. Based on the comparison, a determination is made whether one or more of the electronic components are potentially counterfeit at step 1114. This could include, for example, the analysis system 110 identifying variations in the same characteristic across multiple electronic components in a lot. This could also include the analysis system 110 comparing characteristics of the electronic components being inspected to corresponding characteristics of one or more reference components. Different characteristics could be weighted differently, and a pass/fail indicator or other value could be generated to indicate whether a counterfeited item has been detected. As noted above, a confidence level can be associated with each pass/fail indicator to identify the amount of confidence in the counterfeit decision.

The results of the analysis could then be used in any suitable manner. For example, any component determined to be potentially counterfeit could be marked at step 1116. The marking could take any suitable form, such as a visible marking on the component. Authentic components could be provided for use, while the counterfeit components could be pulled from a lot. Reports could be also be generated, and analysis results could be uploaded to a database 206 or other location for storage and later use.

Although FIG. 11 illustrates one example of a method 1100 for screening electronic components to detect counterfeit articles, various changes may be made to FIG. 11. For example, while shown as a series of steps, various steps in FIG. 11 could overlap, occur in parallel, occur in a different order, or occur multiple times. As a particular example, characteristics of each electronic component being inspected could be compared to characteristics of one or more known good components while each electronic component is being imaged. Once all electronic components in a lot have been imaged, characteristics of the electronic components being inspected can be compared against each other.

It may be advantageous to set forth definitions of certain words and phrases used throughout this patent document. The term "couple" and its derivatives refer to any direct or indirect communication between two or more elements, whether or not those elements are in physical contact with one another. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

Moreover, various functions described above can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:
1. A method comprising:
receiving, from an imaging system, initial information associated with an electronic component captured by the imaging system;
determining a type of the electronic component based on an analysis of the initial information associated with the electronic component;

selecting one or more analysis algorithms based on the determined type of the electronic component, the one or more selected analysis algorithms to be used to verify an authenticity of the electronic component, each analysis algorithm identifying at least one of: a type of data to be analyzed and a manner in which the data is to be collected, each analysis algorithm also defining how the data is to be analyzed to verify the authenticity of the electronic component;

obtaining data associated with the electronic component;

analyzing the data associated with the electronic component using the one or more selected analysis algorithms to determine whether the electronic component is authentic;

calculating a pass/fail indicator for the electronic component based on the analysis, the pass/fail indicator based on multiple characteristics of the electronic component, wherein different characteristics of the electronic component are weighted with different weights when calculating the pass/fail indicator;

generating an output including the pass/fail indicator; and in response to the pass/fail indicator indicating that the electric component is counterfeit, marking the electronic component as counterfeit.

2. The method of claim 1, wherein the one or more selected analysis algorithms include at least one analysis algorithm that compares one or more of the multiple characteristics of the electronic component against one or more characteristics of at least one reference component.

3. The method of claim 2, further comprising:
obtaining the one or more characteristics of the at least one reference component from a database, the database configured to provide characteristics associated with multiple reference components.

4. The method of claim 1, wherein the one or more selected analysis algorithms include at least one analysis algorithm that identifies variations in one or more characteristics of multiple electronic components.

5. The method of claim 1, wherein:
obtaining the data associated with the electronic component comprises obtaining data associated with images of multiple electronic components captured using the imaging system; and the method further comprises at least one of:
operating a transport system to move each electronic component into a position for imaging by the imaging system; and
operating a translation system to move the imaging system into a position for imaging of each electronic component.

6. The method of claim 1, wherein selecting the one or more analysis algorithms comprises at least one of:
identifying a manufacturer and a part number associated with the electronic component based on an image of the electronic component; and
comparing the image of the electronic component to images of reference components to identify at least one reference component most similar to the electronic component, the one or more analysis algorithms selected based on the at least one identified reference component.

7. The method of claim 1, wherein obtaining the data associated with the electronic component comprises obtaining at least one of:
an optical image of the electronic component;
an infrared or X-ray scan of the electronic component; and
an X-ray fluorescence (XRF) spectrographic measurement of the electronic component.

8. The method of claim 1, wherein the one or more selected analysis algorithms include at least one analysis algorithm that identifies one or more of the multiple characteristics of the electronic component, the one or more characteristics including at least one of:
one or more characteristics of markings on the electronic component, the markings including at least one of: a logo, text, and a pin marker;
one or more characteristics of a molded surface of the electronic component;
one or more dimensions of the electronic component; and
one or more characteristics of solder leads of the electronic component.

9. The method of claim 1, wherein selecting the one or more analysis algorithms comprises selecting the one or more analysis algorithms automatically without human intervention.

10. An apparatus comprising:
at least one memory configured to store data associated with an electronic component;
at least one interface configured to receive, from an imaging system, initial information associated with the electronic component captured by the imaging system; and
at least one processing device configured to:
determine a type of the electronic component based on an analysis of the initial information associated with the electronic component;
select one or more analysis algorithms based on the determined type of the electronic component, the one or more selected analysis algorithms to be used to verify an authenticity of the electronic component, each analysis algorithm identifying at least one of: a type of data to be analyzed and a manner in which the data is to be collected, each analysis algorithm also defining how the data is to be analyzed to verify the authenticity of the electronic component;
analyze the data associated with the electronic component using the one or more selected analysis algorithms to determine whether the electronic component is authentic;
calculate a pass/fail indicator for the electronic component based on the analysis, the pass/fail indicator based on multiple characteristics of the electronic component, wherein different characteristics of the electronic component are weighted with different weights when calculating the pass/fail indicator;
generate an output including the pass/fail indicator; and
instruct a marking system to mark the electronic component as counterfeit in response to the pass/fail indicator indicating that the electronic component is counterfeit.

11. The apparatus of claim 10, wherein the one or more selected analysis algorithms include at least one analysis algorithm that compares one or more of the multiple characteristics of the electronic component against one or more characteristics of at least one reference component.

12. The apparatus of claim 10, wherein the one or more selected analysis algorithms include at least one analysis algorithm that identifies variations in one or more characteristics of multiple electronic components.

13. The apparatus of claim 10, further comprising:
the imaging system configured to capture data associated with multiple electronic components; and at least one of:
- a transport system configured to move each electronic component into a position for imaging by the imaging system; and
- a translation system configured to move the imaging system into a position for imaging of each electronic component.

14. The apparatus of claim 13, wherein the imaging system comprises a telecentric imaging system.

15. The apparatus of claim 10, wherein the at least one processing device is configured to calculate the pass/fail indicator using weighted partial least squares (wPLS) calculations.

16. The apparatus of claim 10, wherein the at least one processing device is configured to select the one or more analysis algorithms by at least one of:
- identifying a manufacturer and a part number associated with the electronic component based on an image of the electronic component; and
- comparing the image of the electronic component to images of reference components to identify at least one reference component most similar to the electronic component, the one or more analysis algorithms selected based on the at least one identified reference component.

17. The apparatus of claim 10, wherein the data associated with the electronic component comprises at least one of:
- an optical image of the electronic component;
- an infrared or X-ray scan of the electronic component; and
- an X-ray fluorescence (XRF) spectrographic measurement of the electronic component.

18. A non-transitory computer readable medium containing a computer program, the computer program comprising instructions that, in response to being executed by at least one processing device, cause the at least one processing device to:
- receive, from an imaging system, initial information associated with an electronic component captured by the imaging system;
- determine a type of the electronic component based on an analysis of the initial information associated with the electronic component;
- select one or more analysis algorithms based on the determined type of the electronic component, the one or more selected analysis algorithms to be used to verify an authenticity of the electronic component, each analysis algorithm identifying at least one of: a type of data to be analyzed and a manner in which the data is to be collected, each analysis algorithm also defining how the data is to be analyzed to verify the authenticity of the electronic component;
- obtain data associated with the electronic component;
- analyze the data associated with the electronic component using the one or more selected analysis algorithms to determine whether the electronic component is authentic;
- calculate a pass/fail indicator for the electronic component based on the analysis, the pass/fail indicator based on multiple characteristics of the electronic component, wherein different characteristics of the electronic component are weighted with different weights when calculating the pass/fail indicator;
- generate an output including the pass/fail indicator; and
- instruct a marking system to mark the electronic component as counterfeit in response to the pass/fail indicator indicating that the electronic component is counterfeit.

19. The non-transitory computer readable medium of claim 18, wherein the one or more selected analysis algorithms include at least one analysis algorithm that compares one or more of the multiple characteristics of the electronic component against one or more characteristics of at least one reference component.

20. The non-transitory computer readable medium of claim 18, wherein the one or more selected analysis algorithms include at least one analysis algorithm that identifies variations in one or more characteristics of multiple electronic components.

21. A system comprising:
- handling equipment configured to position electronic components for inspection;
- imaging equipment configured to obtain data associated with each electronic component;
- scanning equipment configured to move at least one of the imaging equipment and the electronic components so that the imaging equipment is able to obtain the data associated with each electronic component; and
- an analysis system configured to:
  - receiving, from the imaging equipment, initial information associated with the electronic components captured by the imaging equipment;
  - determine a type of the electronic components based on an analysis of the initial information associated with the electronic components;
  - select one or more analysis algorithms based on the determined type of the electronic components, the one or more selected analysis algorithms to be used to verify an authenticity of the electronic components, each analysis algorithm identifying at least one of: a type of data to be analyzed and a manner in which the data is to be collected, each analysis algorithm also defining how the data is to be analyzed to verify the authenticity of the electronic components;
  - analyze the data associated with the electronic components using the one or more selected analysis algorithms to determine whether each of the electronic components is authentic;
  - calculate a pass/fail indicator for each of the electronic components based on the analysis, each pass/fail indicator based on multiple characteristics of the corresponding electronic component, wherein different characteristics of the corresponding electronic component are weighted with different weights when calculating the pass/fail indicator;
  - generate an output including the pass/fail indicator; and
  - instruct a marking system to mark the electronic component as counterfeit in response to the pass/fail indicator indicating that the electronic component is counterfeit.

* * * * *